United States Patent
Hashimoto et al.

(10) Patent No.: US 11,065,607 B2
(45) Date of Patent: Jul. 20, 2021

(54) VINYLPYRIDINE RESIN FOR CATALYST SUPPORTS, PRODUCTION METHOD THEREFOR, AND CATALYST FOR METHANOL CARBONYLATION REACTION

(71) Applicant: CHIYODA CORPORATION, Yokohama (JP)

(72) Inventors: Chikako Hashimoto, Yokohama (JP); Ryuichi Kanai, Yokohama (JP); Zhixiong You, Yokohama (JP); Tetsuro Matsumura, Yokohama (JP); Yoichi Umehara, Yokohama (JP)

(73) Assignee: CHIYODA CORPORATION, Kanagawa (JP)

( * ) Notice: Subject to any disclaimer, the term of this patent is extended or adjusted under 35 U.S.C. 154(b) by 238 days.

(21) Appl. No.: 16/084,023

(22) PCT Filed: Mar. 7, 2017

(86) PCT No.: PCT/JP2017/009057
§ 371 (c)(1),
(2) Date: Sep. 11, 2018

(87) PCT Pub. No.: WO2017/159466
PCT Pub. Date: Sep. 21, 2017

(65) Prior Publication Data
US 2020/0290028 A1    Sep. 17, 2020

(30) Foreign Application Priority Data
Mar. 18, 2016 (JP) .............................. JP2016-054644

(51) Int. Cl.
*B01J 31/06* (2006.01)
*B01J 23/46* (2006.01)
(Continued)

(52) U.S. Cl.
CPC ............. *B01J 31/06* (2013.01); *B01J 23/464* (2013.01); *B01J 31/28* (2013.01); *C07C 51/16* (2013.01);
(Continued)

(58) Field of Classification Search
None
See application file for complete search history.

(56) References Cited

U.S. PATENT DOCUMENTS 5,576,458 A * 11/1996 Minami .................. C07C 51/12
562/519
2006/0281944 A1   12/2006 Hosono et al.
2012/0209768 A1*  8/2012 Nuzzi .................... G06Q 40/02
705/44

FOREIGN PATENT DOCUMENTS

EP    0277824 B1    4/1994
EP    2046770 B1    4/2011
(Continued)

OTHER PUBLICATIONS

Notification Concerning Transmittal of International Preliminary Report on Patentability (Form PCT/IB/326) and Notification of Transmittal of Translation of the International Preliminary Report on Patentability (Form PCT/IB/338) issued in counterpart International Application No. PCT/JP2017/009057 dated Sep. 27, 2018, with Forms PCT/IB/373 and PCT/ISA/237. (21 pages).
(Continued)

*Primary Examiner* — Yun Qian
(74) *Attorney, Agent, or Firm* — Westerman, Hattori, Daniels & Adrian, LLP (57) ABSTRACT

A vinylpyridine resin for a catalyst support; a method for producing thereof; and a catalyst for carbonylation of methanol are disclosed. The vinylpyridine resin has: content of nitrogen derived from a pyridine group of 3.00% by mass or more and 8.00% by mass or less; degree of crosslinking of
(Continued)

35% by mole or more and 70% by mole or less; molar ratio C/N of carbon atoms to nitrogen atoms of 12.00 or more and 36.00 or less; total pore volume of 0.20 cc/g or more and 0.45 cc/g or less; specific surface area of 70.0 $m^2$/g or more and 280 $m^2$/g or less; average pore diameter of 5.0 nm or more and 25.0 nm or less; and proportion of a volume of pores having a pore diameter of 10 nm or more to a volume of the whole pores of 4.0% or more and 90.0% or less.

7 Claims, 2 Drawing Sheets (51) Int. Cl.
 *B01J 31/28* (2006.01)
 *C07C 51/16* (2006.01)
 *C08F 126/06* (2006.01)
 *C08J 9/14* (2006.01)
(52) U.S. Cl.
 CPC .............. *C08F 126/06* (2013.01); *C08J 9/141* (2013.01); *B01J 2231/321* (2013.01); *B01J 2531/005* (2013.01); *C08F 2810/20* (2013.01); *C08J 2203/16* (2013.01); *C08J 2339/08* (2013.01)

(56) References Cited

FOREIGN PATENT DOCUMENTS

| EP | 2631010 A1 | 8/2013 |
|---|---|---|
| JP | 47-3334 B | 1/1972 |
| JP | 61-25731 B2 | 6/1986 |
| JP | 63-253047 A | 10/1988 |
| JP | 5-306253 A | 11/1993 |
| JP | 5-306254 A | 11/1993 |
| JP | 6-315637 A | 11/1994 |
| JP | 7-309800 A | 11/1995 |
| JP | 8-92322 A | 4/1996 |
| JP | 2010-502571 A | 1/2010 |
| JP | 2012-81440 A | 4/2012 |
| JP | 2013-035805 A | 2/2013 |
| WO | 2009/134332 A2 | 11/2009 |

OTHER PUBLICATIONS

Office Action dated Apr. 26, 2019, issued in counterpart RU application No. 2018136346, with English translation. (8 pages).
Russian Search Report dated Apr. 25, 2019, issued in counterpart application No. 2018136346, with English translation. (4 pages).
International Search Report w/English translation and Written Opinion in Japanese dated May 23, 2017, issued in counterpart International Application No. PCT/JP2017/009057 (11 pages).
Hamid el al., "4-Vinylpyridine-Ethylene Glycol Dimethacrylate Copolymers. Formation of Porous Structure by Using Cyclohexanone and Toluene as Diluents in Suspension Polymerization", Polymer Journal, 1996, vol. 28, No. 12, pp. 1052-1059, cited in ISR (8 pages).
Maillard-Terrier et al., "Texture Poreuse De Copolymères 4-Vinylpyridine Divinylbenzène", European Polymer Journal, 1984, vol. 20, No. 2, pp. 113-118, cited in ISR (6 pages).
De Santa Maria et al., "Microscopic analysis of porosity of 2-vinylpyridine copolymer networks 1. Influence of diluent", Materials Letters, 2004, vol. 58, No. 5, pp. 563-568, cited in ISR (6 pages).
Malik et al., "Macroporous 4-Vinylpyridine-divinylbenzene—Estimation of Pore Volume, Surface Area, and Pore Size Distribution", e-Polymers, 2006, vol. 6, No. 1, pp. 1-8, cited in ISR (8 pages).
Office Action dated Mar. 23, 2021, issued in counterpart JP Application No. 2018-505840, with English translation. (12 pages).

* cited by examiner

VINYLPYRIDINE RESIN FOR CATALYST SUPPORTS, PRODUCTION METHOD THEREFOR, AND CATALYST FOR METHANOL CARBONYLATION REACTION

TECHNICAL FIELD

The present invention relates to a vinylpyridine resin for a catalyst support, which can be used as a catalyst support for production of acetic acid by carbonylation reaction of methanol.

BACKGROUND ART

Acetic acid is a basic chemical having a wide range of applications of: a raw material for polyvinyl acetate, acetyl cellulose and acetate esters; a solvent for a terephthalic acid production plant; and the like.

As a method for producing acetic acid to be used in chemical industry, a method by, for example, carbonylation of methanol, partial oxidation of acetaldehyde, or oxidation of butane, propane or the like has been known, and at present, most of acetic acid is produced by carbonylation of methanol.

As a method for producing acetic acid by carbonylation of methanol, a "Monsanto process" by reacting methanol with carbon monoxide in a water-containing acetic acid solvent in which a rhodium compound and methyl iodide are homogeneously dissolved (Patent Literature 1) has been well known. Further, in recent years, as a method by the improvement of the Monsanto process, a technique for allowing a reaction to proceed in a heterogeneous system using a catalyst in which rhodium is supported on a porous vinylpyridine resin (Patent Literatures 2 to 5) has been proposed, and has also been put into practical use.

In these improved methods, in addition to the advantage of the Monsanto process in which acetic acid can be produced from methanol in high yield, there are further advantages that the corrosion of an equipment system and the load of a separating and purifying process of a product of acetic acid can be suppressed by lowering the water concentration of a liquid mixture in the reaction system to reduce the amount of the hydroiodic acid produced by hydrolysis of methyl iodide, high concentration of a catalyst is achieved by immobilizing a rhodium complex on vinylpyridine resin to increase the reaction rate, and the cost and load required for the separation and recovery can be suppressed by confining a catalyst in a reactor and reducing precipitation of the catalyst.

As a porous vinylpyridine resin that can be used for these techniques, in Patent Literature 6, a vinylpyridine resin, which is produced by mixing an oil phase containing divinylbenzene as a crosslinking agent, isooctane as a pore forming agent, and benzoyl peroxide as a polymerization initiator in addition to vinylpyridine monomer, with an aqueous phase containing sodium chloride for adjusting the specific gravity and preventing vinylpyridine from being dissolved into an aqueous phase, sodium nitrite for preventing polymerization of the vinylpyridine monomer dissolved in the aqueous phase, and a cellulosic suspension stabilizer for uniformly dispersing the oil phase in the aqueous phase in a polymerization reactor, then polymerizing the resultant mixture at 80° C. for 2 hours, and performing heat treatment at 95° C. for 5 hours, has been disclosed.

In addition, in the production of acetic acid using a heterogeneous catalyst, mainly from the viewpoint of contact efficiency, a stirred tank type reactor, a bubble column type reactor or the like, in which a solid catalyst is fluidized in a reaction solvent to bring the solid catalyst into contact with carbon monoxide, is used. The abrasion (for example, powderizing) of a solid catalyst, which is caused by fluidization movement, and contact with a stirrer, a wall surface or the like of a reactor, is expected to have an influence on the catalyst life and the equipment trouble, therefore, it is required to reduce the abrasion as small as possible. In Patent Literature 7, a vinylpyridine resin for a catalyst support, in which powderizing is suppressed with the improvement of the abrasion resistance by controlling the volume ratio of pores having a size of 3 to 5 nm, or the like, and a method for producing thereof have been disclosed. The vinylpyridine resin disclosed in Patent Literature 7 has sufficient specific surface area, pore volume, average pore diameter, heat resistance, and abrasion resistance, for being able to be used as a catalyst support for carbonylation of methanol.

CITATION LIST

Patent Literature

PTL 1: Japanese Patent Application Publication No. 47-3334
PTL 2: Japanese Patent Application Laid-Open No. 63-253047
PTL 3: Japanese Patent Application Laid-Open No. 5-306253.
PTL 4: Japanese Patent Application Laid-Open No. 5-306254
PTL 5: Japanese Patent Application Laid-Open No. 6-315637
PTL 6: Japanese Patent Application Publication No. 61-25731
PTL 7: Japanese Patent Application Laid-Open No. 2012-81440

SUMMARY OF INVENTION

Technical Problem

However, there is a constant demand for a more economical process with large capacity of production, and also in the carbonylation reaction of methanol using a heterogeneous catalyst, the improvement of the reaction rate, and the further prolongation of catalyst life have been expected.

In order to improve the heat resistance and abrasion resistance of a vinylpyridine resin, it is conceivable to increase the degree of crosslinking. However, when the degree of crosslinking is increased, the pore diameter is generally decreased due to an increase in the rate of polymerization, a decrease in the degree of flexibility of a resin structure, or the like, that is, there is a tendency that the distribution of pore diameter is shifted toward the smaller size side, therefore, a problem that the activity of a catalyst is lowered is caused. In addition, the content of pyridine groups in a vinylpyridine resin is decreased when the degree of crosslinking is increased, which also causes a problem of lowering the catalytic activity.

For example, the relationship between the degree of crosslinking and catalytic activity of a vinylpyridine resin has been studied in detail in the examples of Patent Literature 5, and it is indicated that when the degree of crosslinking is changed from 17% by mole to 28% by mole, the heat resistance of the vinylpyridine resin is improved and the decomposition rate (denitrification rate) is drastically lowered, and the catalytic activity drops to around 40%.

In view of the problems described above, an object of the present invention is to provide a vinylpyridine resin for a catalyst support, which is excellent in the heat resistance, the abrasion resistance, and the activity of a catalyst in which rhodium is supported; a method for producing thereof; and a catalyst for carbonylation of methanol.

Solution to Problem

Based on the result of earnest research, the present inventors found that the above object can be achieved by a vinylpyridine resin that satisfies a content of nitrogen derived from a vinylpyridine group of 3.00% by mass or more and 8.00% by mass or less; a degree of crosslinking of 35% by mole or more and 70% by mole or less; a molar ratio C/N of carbon atoms to nitrogen atoms of 12.00 or more and 36.00 or less; a total pore volume of 0.20 cc/g or more and 0.45 cc/g or less; a specific surface area of 70.0 $m^2$/g or more and 280.0 $m^2$/g or less; an average pore diameter of 5.0 nm or more and 25.0 nm or less; and a proportion of a volume of pores having a pore diameter of 10 nm or more to a volume of the whole pores of 4.0% or more and 90.0% or less, and thus completed the present invention.

The vinylpyridine resin for a catalyst support according to the present invention has: a content of nitrogen derived from a pyridine group of 3.00% by mass or more and 8.00% by mass or less; a degree of crosslinking of 35% by mole or more and 70% by mole or less; a molar ratio C/N of carbon atoms to nitrogen atoms of 12.00 or more and 36.00 or less; a total pore volume of 0.20 cc/g or more and 0.45 cc/g or less; a specific surface area of 70.0 $m^2$/g or more and 280.0 $m^2$/g or less; an average pore diameter of 5.0 nm or more and 25.0 nm or less; and a proportion of a volume of pores having a pore diameter of 10 nm or more to a volume of the whole pores of 4.0% or more and 90.0% or less.

The above-described vinylpyridine resin for a catalyst support is preferably a copolymer of vinylpyridine and divinylbenzene.

The method for producing a vinylpyridine resin for a catalyst support according to the present invention includes: mixing an oil medium containing vinylpyridine, a crosslinking agent, a pore forming agent and a polymerization initiator, and an aqueous medium; and subjecting the resultant mixture to suspension polymerization, wherein the polymerization initiator contains a main polymerization initiator, and an auxiliary polymerization initiator having a half-life temperature lower than a half-life temperature of the main polymerization initiator, the auxiliary polymerization initiator is 0.25% by mass or less relative to the total amount of monomers, and the pore forming agent contains two or more kinds of organic solvents, and an absolute value of difference between a SP value of the vinylpyridine resin for a catalyst support and a SP value of the pore forming agent is 1.80 or more and 2.80 or less.

The above-described main polymerization initiator is 1.50% by mass or less relative to the total amount of monomers.

Further, the pore forming agent preferably contains an organic solvent having a benzene ring.

In addition, it is preferred that the auxiliary polymerization initiator has a half-life temperature lower than the temperature of the suspension polymerization, and the main polymerization initiator has a half-life temperature higher than the temperature of the suspension polymerization.

The catalyst for carbonylation of methanol according to the present invention is characterized by supporting rhodium on the above-described vinylpyridine resin as a catalyst support.

In the above-described catalyst for carbonylation of methanol, the thermal decomposition rate in a mixture of 86.5% by mass of acetic acid, 8.0% by mass of methyl iodide, and 5.5% by mass of water under the condition of 220° C. in a nitrogen atmosphere is preferably 0.25% by mole or less per hour.

Advantageous Effects of Invention

According to the present invention, a vinylpyridine resin for a catalyst support, which is excellent in the heat resistance, the abrasion resistance, and the catalytic activity, can be provided. In addition, the catalyst in which rhodium is supported on this vinylpyridine resin as a catalyst support is excellent in the heat resistance, the abrasion resistance, and the catalytic activity, and therefore can be suitably used for producing acetic acid.

DESCRIPTION OF EMBODIMENTS

The vinylpyridine resin for a catalyst support according to the present invention is a vinylpyridine resin having a content of the nitrogen derived from vinylpyridine groups of 3.00% by mass or more and 8.00% by mass or less, a degree of crosslinking of 35% by mole or more and 70% by mole or less, a molar ratio C/N of carbon atoms to nitrogen atoms of 12.00 or more and 36.00 or less, a total pore volume of 0.20 cc/g or more and 0.45 cc/g or less, a specific surface area of 70.0 $m^2$/g or more and 280.0 $m^2$/g or less, an average pore diameter of 5.0 nm or more and 25.0 nm or less, and a proportion of the volume of pores having a pore diameter of 10 nm or more to the volume of the whole pores of 4.0% or more and 90.0% or less.

The vinylpyridine resin for a catalyst support according to the present invention as described above (hereinafter, also simply referred to as "vinylpyridine resin") is, as shown in Examples described later, excellent in the heat resistance and the abrasion resistance, and further the catalyst in which rhodium is supported is excellent in the catalytic activity in carbonylation reaction of methanol. For example, the catalyst using the vinylpyridine resin according to the present invention as a support has high abrasion resistance, and the abrasion resistance is hardly decreased until the decomposition ratio (nitrogen reduction ratio) reaches around 25%, therefore, a stirred tank type reactor or a bubble column type reactor, in which a catalyst is fluidized to bring the catalyst into contact with carbon monoxide, can also be used even at the decomposition ratio of around 25%. In a stirred tank type reactor in which the reaction mixture is stirred with a stirrer arranged in the reactor in order to fluidize a catalyst, or in a bubble column type reactor in which bubbles are fed into the reactor to stir the reaction mixture, the catalyst tends to abrade due to the collision with the stirrer, the bubbles and the wall surface of the reactor, or due to the fluidization movement of the reaction mixture, however, since the vinylpyridine resin according to the present invention is excellent in the abrasion resistance, the stirred tank type reactor or the bubble column type reactor can be suitably used. In addition, a catalyst using the vinylpyridine resin according to the present invention as a support is excellent in the heat resistance, and therefore can be used under high temperature. Further, the catalyst is also excellent in the activity in carbonylation reaction of methanol, and therefore can allow the reaction to proceed efficiently to obtain acetic acid. In this regard, the catalytic activity is hardly decreased until the decomposition ratio reaches around 25%. On the other hand, in a case where even one of the above-described requirements of the present invention is not satisfied, the effect of the present invention, which is excellent in all of the above heat resistance, the abrasion resistance and the catalytic activity, cannot be obtained.

Herein, as described above, in order to improve the heat resistance and abrasion resistance of the vinylpyridine resin, it is conceivable to increase the degree of crosslinking. However, the rate of polymerization is increased when the degree of crosslinking is increased, or in general, there is a tendency that the pore diameter is decreased due to the decrease in degree of flexibility of a resin structure, or the like, therefore, a problem that the activity of a catalyst is lowered is caused. In addition, when the use ratio of a crosslinking agent is increased in order to increase the degree of crosslinking, for example, in a case where a crosslinking agent having no pyridine group is used, the content of the pyridine groups in the vinylpyridine resin is decreased, and the molar ratio of iodine (quaternized pyridine group)/rhodium becomes small, therefore, the rhodium complex becomes unstable, and which also causes a problem of lowering the catalytic activity.

In the present invention, by using a vinylpyridine resin satisfying all of the above-described specific requirements, a vinylpyridine resin in which the heat resistance and the abrasion resistance are improved, and the catalytic activity can also be improved can be provided.

As will be described in detail later, when a vinylpyridine resin is produced by subjecting raw material monomers (that is, vinylpyridine, a crosslinking agent and the like) to suspension polymerization reaction in the presence of a pore forming agent, by setting the amount of an auxiliary polymerization initiator to a small amount of 0.25% by mass or less relative to the total amount of the monomers, the monomers are polymerized so as not to increase the rate of polymerization. Further, by using a crosslinking agent of which the coexisting impurities are reduced and the purity is high, a vinylpyridine resin, which has, while maintaining the high degree of crosslinking of 35% by mole or more and 70% by mole or less, a content of the nitrogen derived from pyridine groups of 3.00% by mass or more and 8.00% by mass or less, a molar ratio C/N of carbon atoms to nitrogen atoms of 12.00 or more and 36.00 or less, a total pore volume of 0.20 cc/g or more and 0.45 cc/g or less, a specific surface area of 70.0 m²/g or more and 280.0 m²/g or less, an average pore diameter of 5.0 nm or more and 25.0 nm or less, and a proportion of the volume of pores having a pore diameter of 10 nm or more to the volume of the whole pores of 4.0% or more and 90.0% or less, and in which the heat resistance and the abrasion resistance are improved and the catalytic activity is also improved, can be obtained.

In the present specification, the expression "specific surface area" is a specific surface area calculated from the amount of adsorption of nitrogen gas by using Brunauer-Emmett-Teller (BET) adsorption isotherm equation, and is measured by a three-point method using liquid nitrogen with the use of "AUTOSORB-1" manufactured by Yuasa Ionics Co., Ltd.

The expression "average pore diameter" is measured by a three-point method using liquid nitrogen with the use of "AUTOSORB-1" manufactured by Yuasa Ionics Co., Ltd. In the present invention, the expression "average pore diameter (D)" means a representative diameter when all of the pores are represented by one cylindrical pore. Specifically, the average pore diameter (D) can be calculated only from two physical property values of specific surface area (A) and total pore volume (V) by using the following equation.

$$D = 4V/A$$

The expression "total pore volume" is the sum of all of the pore volumes, and is measured by a three-point method using liquid nitrogen with the use of "AUTOSORB-1" manufactured by Yuasa Ionics Co., Ltd.

The expression "proportion of the volume of pores having a pore diameter of 10 nm or more to the volume of the whole pores" is a value obtained by dividing the expression "total volume of pores having a pore diameter of 10 nm or more" by the expression "total pore volume". The expression "total volume of pores having a pore diameter of 10 nm or more" is also measured by a three-point method using liquid nitrogen with the use of "AUTOSORB-1" manufactured by Yuasa Ionics Co., Ltd.

The expression "content of the nitrogen derived from vinylpyridine groups" is a proportion of the total amount of the nitrogen atoms derived from the vinylpyridine groups in the vinylpyridine resin according to the present invention, and is a value obtained by determining the total mass of the nitrogen derived from the vinylpyridine groups in the vinylpyridine resin by elemental analysis and by dividing the total mass of the nitrogen by the mass of the vinylpyridine resin. The content of the nitrogen derived from vinylpyridine groups is measured by a CHN corder.

The expression "molar ratio C/N of carbon atoms to nitrogen atoms" is a value obtained by determining the total number of moles C of carbon atoms and the total number of moles N of nitrogen atoms in the vinylpyridine resin by elemental analysis and by dividing the C by the N, and measured by a CHN corder.

The expression "degree of crosslinking" is a value calculated by the following equation.

$$\text{Degree of crosslinking (\% by mole)} = A/B \times 100$$

A: the number of moles of a crosslinking agent (compound having two or more reactive sites of a vinyl group or the like) used for synthesis of a vinylpyridine resin
B: the total number of moles of monomers used for synthesis of a vinylpyridine resin In the vinylpyridine resin according to the present invention, the content of the nitrogen derived from vinylpyridine groups is preferably 3.00% by mass or more and 8.00% by mass or less. The degree of crosslinking is preferably 40% by mole or more and 70% by mole or less. In addition, the molar ratio C/N of carbon atoms to nitrogen atoms is preferably 14.00 or more and 30.00 or less. Further, the total pore volume is preferably 0.20 cc/g or more and 0.40 cc/g or less.

In addition, in the vinylpyridine resin according to the present invention, with respect to the pore diameter, it is preferred that the requirement that the proportion of the volume of the pores having an average pore diameter of 5.0 nm or more and 25.0 nm or less and a pore diameter of 10 nm or more to the volume of the whole pores is 4.0% or more and 90.0% or less is satisfied, and further the vinylpyridine resin is a resin containing an appropriate amount of pores having a pore diameter of 2.0 nm or less. For example, the proportion of the specific surface area of only the pores having a pore diameter of 2.0 nm or less to the specific surface area of the vinylpyridine resin (that is, the specific surface area of the whole vinylpyridine resin) is 10% or more and 70% or less, and preferably 12% or more and 60% or less.

For the high activity, the diffusion of substances in pores (that is, causing carbonylation reaction in pores and discharging the produced acetic acid out of the pores) is required to be easy. For that purpose, it is required that the proportion of the volume of the pores having a large pore size to some extent, specifically, having an average pore diameter of 5.0 nm or more and 25.0 nm or less and a pore diameter of 10 nm or more to the volume of the whole pores is 4.0% or more and 90.0% or less. On the other hand, the rhodium carbonyl complex that is an active species of carbonylation reaction is observed as a dimer (diameter 1 nm×height 1 nm or so). In addition, the pore diameter effective for the reaction is considered to be 2 to 3 times or less of the molecule, that is, roughly 2.0 nm or less. Further, when the pore diameter is 2 to 3 times larger than the molecule, the potential becomes the most stable due to the wall effect, therefore, the pores having a pore diameter of 2.0 nm or less are considered to contribute largely to the activity. Accordingly, it is preferred that the vinylpyridine resin according to the present invention has an average pore diameter of 5.0 nm or more and 25.0 nm or less, a proportion of the volume of pores having a pore diameter of 10 nm or more to the volume of the whole pores of 4.0% or more and 90.0% or less, and a proportion of the specific surface area of only the above-described pores having a pore diameter of 2.0 nm or less of 10% or more and 70% or less.

In addition, the vinylpyridine resin for a catalyst support according to the present invention is preferably spherical, and the particle diameter is preferably 50 to 1000 μm, and more preferably 150 to 750 μm. The particle diameter can be determined by a laser diffraction method.

As the vinylpyridine resin according to the present invention, any vinylpyridine resin may be used as long as it satisfies the above-described requirements, and each value may be set to a desired value depending on the characteristics required within the range of the requirements. For example, in a case where the long service life of the catalyst is particularly required, the content of the nitrogen derived from pyridine groups is lowered to around 3.00% by mass, and the C/N is increased as much as possible. Further, in a case where a higher catalytic activity is required even if the catalyst life is relatively shortened, the C/N is set to be around 12.00, and the content of the nitrogen derived from pyridine groups is set to be around 8.00% by mass.

The vinylpyridine resin for a catalyst support according to the present invention can be produced, for example, by a method for producing a vinylpyridine resin for a catalyst support including: mixing an oil medium containing vinylpyridine, a crosslinking agent, a pore forming agent and a polymerization initiator, and an aqueous medium to disperse droplets of the oil medium in the aqueous medium; and performing the suspension polymerization, in which the polymerization initiator contains a main polymerization initiator and an auxiliary polymerization initiator having a half-life temperature lower than that of the main polymerization initiator, the auxiliary polymerization initiator is 0.25% by mass or less relative to the total amount of monomers, the pore forming agent contains two or more kinds of organic solvents, and an absolute value of difference between the solubility parameter (SP) value of the vinylpyridine resin for a catalyst support to be obtained and the SP value of the pore forming agent is 1.80 or more and 2.80 or less.

The monomers to be subjected to suspension polymerization are vinylpyridine and a crosslinking agent (crosslinkable monomer). As long as the above-described physical properties are satisfied, other monomers may be copolymerized in addition to the vinylpyridine and the crosslinking agent.

As the vinylpyridine, although it is not limited to the following, 2-vinylpyridine; 3-vinylpyridine; 4-vinylpyridine; a 4-vinylpyridine derivative, a 2-vinylpyridine derivative or the like, which has a lower alkyl group such as a methyl group or an ethyl group on the pyridine ring; 2-methyl-5-vinylpyridine; 2-ethyl-5-vinylpyridine; 3-methyl-5-vinylpyridine; 2,3-dimethyl-5-vinylpyridine; 2-methyl-3-ethyl-5-vinylpyridine; or the like can be used. These monomers may be used alone, or two or more kinds thereof may be used. The amount of the vinylpyridine is preferably 20% by mole or more and 65% by mole or less relative to the total amount of the monomers. This is because there is a tendency that when the vinylpyridine is less than 20% by mole, the molar ratio of iodine (by quaternized pyridine group)/rhodium becomes small in a catalyst, the rhodium complex becomes unstable, and the catalytic activity is decreased, and when the vinylpyridine is higher than 65% by mole, the crosslinking structure required for obtaining physical stability such as heat resistance becomes insufficient.

The crosslinking agent is a compound having two or more reactive sites of a vinyl group or the like, and a compound having two or more vinyl groups is preferred. Examples of the compound having two or more vinyl groups include a compound containing no nitrogen, for example, an aromatic polyvinyl compound such as divinylbenzene, divinyltoluene, divinylnaphthalene, or trivinylbenzene, or an aliphatic polyvinyl compound such as butadiene, diallyl phthalate, ethylene glycol diacrylate, or ethylene glycol dimethacrylate; divinylpyridine; and trivinylpyridine. In addition, the amount of the crosslinking agent to be used is 35% by mole or more and 70% by mole or less, and preferably 40% by mole or more and 70% by mole or less relative to the total amount of monomers.

As other monomers, a monomer having one vinyl group such as ethylvinylbenzene, and styrene can be mentioned. However, in the present invention, it is preferred that the amount of the crosslinking agent such as divinylbenzene is large, and the other monomers are used in a small amount or are not used. Herein, the crosslinking agent (for example, divinylbenzene) is a compound having two or more reactive sites of a vinyl group or the like, and a compound having only one crosslinking site generated as an impurity during synthesis (for example, other monomers such as ethylvinylbenzene) also generally coexists with the crosslinking agent. In a case where such a crosslinking agent coexisting with impurities is used, when the use ratio of the crosslinking agent is increased, the degree of crosslinking can be increased, however, the content of the vinylpyridine groups is lowered as compared with that in a case where the degree of crosslinking is increased by using a crosslinking agent in which the amount of impurities is reduced and of which the purity is high. Accordingly, in the present invention, in order to increase the abrasion resistance and the heat resistance, a crosslinking agent in which the amount of impurities is reduced and of which the purity is high is used, that is, by setting the amount of other monomers to be 3.0% by mole or less relative to the total amount of monomers, while maintaining the high degree of crosslinking of 35% by mole or less and 70% by mole or more, the content of the nitrogen derived from pyridine groups is 3.00% by mass or more and 8.00% by mass or less to obtain also high catalytic activity.

These monomers are mixed at a ratio so that a vinylpyridine resin to be produced has a content of the nitrogen derived from vinylpyridine groups of 3.00% by mass or more and 8.00% by mass or less, a degree of crosslinking of 35% by mole or more and 70% by mole or less, and a molar ratio C/N of carbon atoms to nitrogen atoms of 12.00 or more and 36.00 or less. Subsequently, into the obtained mixture, a pore forming agent (porous agent) and a polymerization initiator are added to obtain an oil medium.

The expression "pore forming agent" as used in the present invention means a solvent that dissolves monomers but hardly dissolves a polymer formed by polymerizing monomers.

When the vinylpyridine resin is synthesized by a suspension polymerization method, the pore forming agent charged together with monomers and the produced polymer are phase-separated in droplets of the oil medium, and numerous microgels having crosslinked network structure are generated. By removing the pore forming agent existing in gaps between the microgels after the suspension polymerization, the vinylpyridine resin to be obtained has pores. The size of the microgels, the adhesion between the microgels, or the distribution of an organic solvent in gaps of the microgels, that can affect the pore size or the like of the pores possessed in the vinylpyridine resin to be obtained, are remarkably affected by the compatibility between the microgels and the pore forming agent. The compatibility between the polymer (vinylpyridine resin) and the pore forming agent is affected by both of the polarities, and the closer the polarities are to each other, the higher the compatibility is.

As such a pore forming agent, in the present invention, two or more kinds of organic solvents are used. Further, one in which an absolute value of difference (hereinafter, also referred to as "SP absolute difference") between the SP value of the vinylpyridine resin for a catalyst support (polymer) and the SP value of the pore forming agent, which is indicated by the following equation, is 1.80 or more and 2.80 or less is used as the pore forming agent. The SP value is a solubility parameter indicated by the square root of the cohesive energy density representing the intermolecular force, and is determined by a Fedors method. The SP value of the pore forming agent is a value obtained by multiplying the SP value of each organic solvent constituting the pore forming agent by the content of the organic solvent to the pore forming agent on a volume basis, and summing the value obtained for each organic solvent. Specifically, for example, in a case where the pore forming agent includes three kinds of organic solvents (first organic solvent, second organic solvent, and third organic solvent), the SP value can be determined by the following equation in general.

*SP* absolute difference=|*SP* value of vinylpyridine resin for a catalyst support–*SP* value of pore forming agent|

*SP* value of pore forming agent=(*SP* value of first organic solvent×(volume of first organic solvent/volume of pore forming agent))+(*SP* value of second organic solvent×(volume of second organic solvent/volume of pore forming agent))+(*SP* value of third organic solvent×(volume of third organic solvent/volume of pore forming agent))

As the organic solvent constituting the pore forming agent, for example, an organic solvent having a property of swelling a crosslinked copolymer (that is, the vinylpyridine resin according to the present invention), a non-swelling organic solvent, or the like can be used. Specific examples of the organic solvent include trimethylbenzene, toluene, xylene, 2-ethylhexanol, dioctyl phthalate, octane, nonane, and n-dodecane. The pore forming agent preferably contains an organic solvent having a benzene ring such as trimethylbenzene, toluene, or xylene. Due to the compatibility between the benzene ring of the organic solvent contained in the pore forming agent and the aromatic ring of the copolymer including vinylpyridine, a crosslinking agent, and other monomers to be polymerized as needed, the organic solvent having the benzene ring is uniformly distributed in the network structure of a microgel and in the gaps between microgels, therefore, the nonuniformity of a structure of the vinylpyridine resin to be obtained is prevented, and the powderizing or thermal decomposition can be suppressed.

The pore forming agent is prepared by using at least one of trimethylbenzene and toluene and at least one selected from octane, dioctyl phthalate and n-dodecane, and the mass ratio is preferably as follows: total mass of trimethylbenzene and toluene:total mass of octane, dioctyl phthalate and n-dodecane=1:0.1 to 9.0.

The total amount of the pore forming agent is preferably 5% by mass or more and 50% by mass or less, and more preferably 10% by mass or more and 30% by mass or less relative to the oil medium.

Note that the pore forming agent is removed by heating, distillation, solvent extraction, or the like after the suspension polymerization reaction.

The polymerization initiator is required to use both of a main polymerization initiator, and an auxiliary polymerization initiator having a half-life temperature lower than that of the main polymerization initiator. In the auxiliary polymerization initiator used in the present invention has, for example, a 10-hour half-life temperature lower by around 10 to 35° C. than that of the main polymerization initiator, and the 10-hour half-life temperature is 40 to 65° C. In addition, the amount of the auxiliary polymerization initiator to be used is required to be 0.25% by mass or less relative to the total amount of monomers. By reducing the amount of the auxiliary polymerization initiator to 0.25% by mass or less relative to the total amount of monomers as mentioned above, the suspension polymerization reaction performed in the presence of a pore forming agent starts and progresses relatively moderately. That is, the monomers can be polymerized so as not to increase the rate of polymerization. For this reason, the decrease in the pore diameter is suppressed in spite of high degree of crosslinking, and a vinylpyridine resin having the pores having a large pore size to some extent, which contributes to the diffusion in the pores, specifically, a vinylpyridine resin having a proportion of the volume of pores having a pore diameter of 10 nm or more to the volume of the whole pores of 4.0% or more and 90.0% or less can be produced. Therefore, there is no problem of decrease in the catalytic activity due to the decrease in pore diameter, and the vinylpyridine resin that is excellent in the heat resistance, the abrasion resistance, and the catalytic activity is obtained. For example, the heat resistance and the abrasion resistance under methanol carbonylation reaction conditions are drastically improved, and further sufficient catalytic activity is maintained even if the decomposition proceeds to the limit of the physical strength as a catalyst used for a fluidized bed.

The main polymerization initiator to be used in the present invention is not particularly limited, and any of those that have been conventionally used for initiating the reaction of a vinyl compound, such as benzoyl peroxide and lauroyl peroxide, can be used. These may be used alone, or in combination of two or more kinds thereof.

The amount of the main polymerization initiator to be used is not also particularly limited, but if the main polymerization initiator remains, there is a possibility that the catalytic activity and the catalyst lifetime are adversely affected, therefore, it is preferred to set the amount to be a minimized amount only needed to complete the polymerization. In addition, since the rate of polymerization is increased, the pore diameter tends to be decreased. Accordingly, the amount of the main polymerization initiator to be used is suitably 0.10% by mass or more and 1.50% by mass or less relative to the total amount of monomers.

The auxiliary polymerization initiator used in the present invention is a polymerization initiator having a half-life temperature lower than that of the main polymerization initiator. As the auxiliary polymerization initiator, an azo-based polymerization initiator, for example, an azonitrile compound such as 2,2'-azobis(4-methoxy-2,4-dimethylvaleronitrile), 2,2'-azobis(2,4-dimethylvaleronitrile), 2,2'-azobis(isobutyronitrile), and 2,2'-azobis(2-methylbutyronitrile); or an organic peroxide, for example, peroxydicarbonates such as diisopropyl peroxycarbonate, and di-n-propyl peroxycarbonate, or peroxy esters such as t-hexyl peroxypivalate, and t-butyl peroxyneodecanoate can be used. These may be used alone, or in combination of two or more kinds thereof. The amount of the auxiliary polymerization initiator to be used is 0.25% by mass or less, and preferably 0.05% by mass or more and 0.15% by mass or less relative to the total amount of monomers.

In addition, it is preferred that as the auxiliary polymerization initiator, one having a half-life temperature lower than the temperature of suspension polymerization, and as the main polymerization initiator, one having a half-life temperature higher than the temperature of suspension polymerization. By using one having a half-life temperature lower than the temperature of suspension polymerization as the auxiliary polymerization initiator, an oligomer to form a core can be generated before starting polymerization as a whole. Since the main polymerization initiator has a role of growing the polymer, by using one having a half-life temperature higher than the polymerization temperature as the main polymerization initiator, radical generation can be continued little by little until the polymerization is completed.

In this regard, two or more kinds of pore forming agents or polymerization initiators, which has been prepared by mixing the agents or the initiators in advance, may be used, or may be mixed by stirring or the like in a reactor.

By subjecting monomers to suspension polymerization in an aqueous medium by using such an oil medium, the vinylpyridine resin to be obtained can be made to have a content of the nitrogen derived from vinylpyridine groups of 3.00% by mass or more and 8.00% by mass or less, a degree of crosslinking of 35% by mole or more and 70% by mole or less, a molar ratio C/N of carbon atoms to nitrogen atoms of 12.00 or more and 36.00 or less, a total pore volume of 0.20 cc/g or more and 0.45 cc/g or less, a specific surface area of 70.0 m$^2$/g or more and 280.0 m$^2$/g or less, an average pore diameter of 5.0 nm or more and 25.0 nm or less, and a proportion of the volume of pores having a pore diameter of 10 nm or more to the volume of the whole pores of 4.0% or more and 90.0% or less. By adjusting the balance of individual production conditions such as the ratio of each of monomers, a pore forming agent and an auxiliary polymerization initiator, a vinylpyridine resin having a desired content of the nitrogen derived from vinylpyridine groups, a desired degree of crosslinking, a desired molar ratio C/N of carbon atoms to nitrogen atoms, a desired total pore volume, a desired proportion of pores having a size of 10 nm or more, a desired specific surface area, and a desired average pore diameter can be produced. For example, by changing the amount of the auxiliary polymerization initiator, and the combination, amount and ratio of the pore forming agent, the average pore diameter can be adjusted, and further by changing the molar ratio C/N of carbon atoms to nitrogen atoms and the amount of the auxiliary polymerization initiator, the heat resistance can be adjusted.

The aqueous medium used in the present invention is not particularly limited as long as it can be used in combination with an oil medium and perform suspension polymerization of monomers in the oil medium, and for example, the aqueous medium is a liquid in which a dispersion stabilizer (suspension stabilizer), a surfactant, a radical scavenger, a specific gravity adjuster, a pH adjusting agent and the like are dissolved or dispersed in water.

A dispersion stabilizer that can be used in the present invention is not also particularly limited, and a water-soluble polymer such as polyvinyl alcohol, hydroxyethyl cellulose, carboxymethyl cellulose, sodium polymethacrylate, sodium polyacrylate, starch, gelatin, and an ammonium salt of a styrene/maleic anhydride copolymer, and an inorganic salt such as calcium carbonate, calcium sulfate, bentonite, and magnesium silicate, which have been conventionally used, can be used.

A surfactant, a radical scavenger, a specific gravity adjuster, and a pH adjusting agent, which can be used in the present invention are not also particularly limited, and any of those that have been conventionally used can be used. For example, dodecylbenzenesulfonic acid or the like as the surfactant, sodium nitrite or the like as the radical scavenger, sodium chloride, sodium carbonate, sodium sulfate or the like as the specific gravity adjuster, and sodium hydroxide or the like as the pH adjusting agent can be used.

The temperature at which suspension polymerization is performed may be a temperature at which polymerization reaction proceeds, and if the temperature is extremely low, dissolution of the specific gravity adjuster or dispersion stabilizer to be added to an aqueous medium becomes insufficient. Further, it is conceivable that when the temperature exceeds 80° C., the temperature is partially increased due to heat of polymerization, boiling is caused, and dispersion of the oil medium becomes unstable. For example, in a case where an azo-based polymerization initiator (10-hour half-life temperature of 30 to 67° C.) is used, the temperature of 25 to 80° C. is suitably used. Specifically, for example, the temperature is slowly raised to polymerize the polymer at a temperature of 50 to 80° C., and then further raised to apply a heat treatment at 85° C. to 95° C., and the vinylpyridine resin according to the present invention can be produced. Further, the reaction time for suspension polymerization is, for example, 2 to 6 hours, and the heat treatment time is 3 to 20 hours.

In addition, it is preferred that the generated heat of polymerization is removed as much as possible to keep the reaction temperature constant. This is because there is a risk that the liquid temperature is increased due to the heat of polymerization reaction and the dispersion of the oil medium becomes unstable, further the generation of radicals are increased due to the temperature rise, resulting in increase in the number of the generated oligomers that become cores, and the molecular weight of the polymer to form a resin becomes small.

The vinylpyridine resin for a catalyst support according to the present invention described above is excellent in the heat resistance and the abrasion resistance as compared with those of conventional products, and further has the pores with which the diffusion of substances is easy and the active species are stabilized, therefore, the rhodium catalyst supported on the vinylpyridine resin has high activity. Accordingly, the rate of methanol carbonylation reaction can be improved, and further the lifetime of the catalyst is prolonged, therefore, the economic efficiency of the processes can be improved.

By supporting rhodium on the vinylpyridine resin for a catalyst support according to the present invention, the catalyst for carbonylation of methanol according to the present invention can be obtained. The vinylpyridine resin for a catalyst support according to the present invention is excellent in the heat resistance and the abrasion resistance, and further is excellent in the catalytic activity. Accordingly, a catalyst in which rhodium is supported on the vinylpyridine resin is also excellent in the heat resistance, the abrasion resistance, and the catalytic activity. For example, a thermal decomposition rate in a mixture of 86.5% by mass of acetic acid, 8.0% by mass of methyl iodide, and 5.5% by mass of water under the condition of 220° C. in a nitrogen atmosphere can be set to 0.25% by mole or less per hour.

The method for supporting rhodium on the vinylpyridine resin is not particularly limited, and for example, by bringing a vinylpyridine resin into contact with a rhodium halide or a rhodium salt such as rhodium acetate under a carbon monoxide pressure (0.7 to 3 MPa) in a solution containing methyl iodide, the rhodium can be supported on the vinylpyridine resin. At this time, the nitrogen atoms of the vinylpyridine groups in the vinylpyridine resin are quaternized, and rhodium complex ions formed by the reaction among the rhodium halide, methyl iodide and carbon monoxide, that is, ions of rhodium carbonyl complex $[Rh(CO)_2I_2]^-$ are adsorbed to the quaternized vinylpyridine resin in an ion-exchange manner, and a solid catalyst for carbonylation of methanol according to the present invention can be obtained. The amount of the rhodium to be supported is not particularly limited, and can be set to around 0.2 to 5.0% by mass relative to the amount of the vinylpyridine resin.

By reacting methanol and carbon monoxide in a reaction mixture with the use of such a catalyst for carbonylation of methanol, acetic acid can be produced. Such a method for producing acetic acid includes, for example, a reaction step of reacting methanol (carbonylation raw material) with carbon monoxide to produce acetic acid (carbonyl compound) in a reaction mixture containing the catalyst for carbonylation of methanol according to the present invention, and a distillation step of distilling the reaction product solution from the reaction step to recover a gas (vapor) phase fraction containing acetic acid (carbonyl compound).

Figure 1:
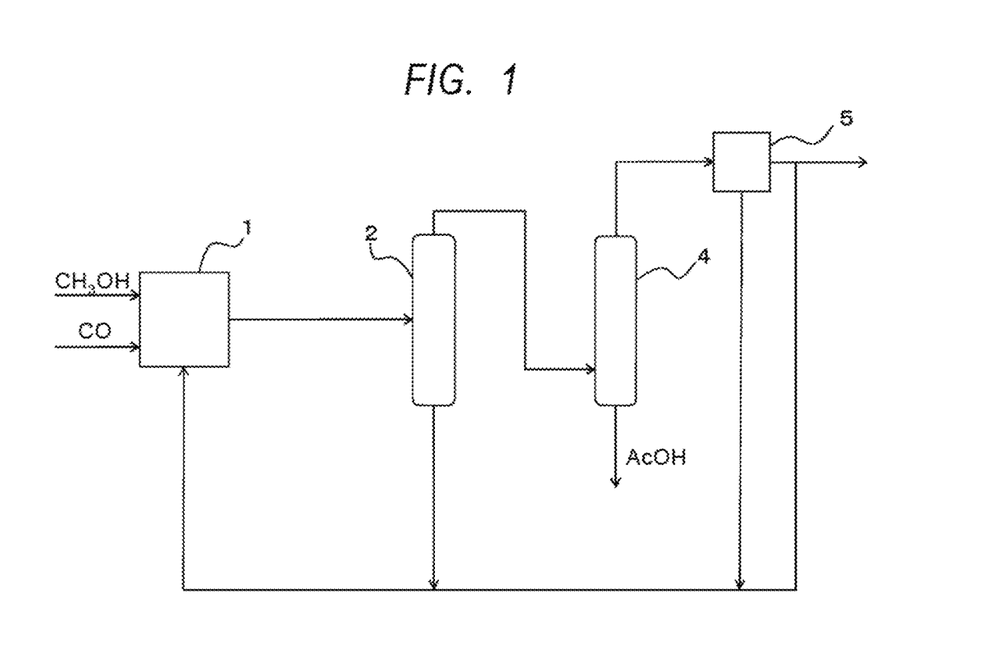
FIG. 1 is a schematic diagram showing one example of an equipment system for producing acetic acid.

FIG. 1 is a schematic diagram showing an equipment system for producing acetic acid in which production of acetic acid by carbonylation of methanol can be performed. As shown in FIG. 1, the equipment system for producing acetic acid is mainly provided with a carbonylation reactor 1 as a reaction step, a flasher 2 performing a flash evaporation process and a light end distillation column 4 performing a light end separation process as a distillation step, and a decanter 5 as a standing step.

Methanol and carbon monoxide as the carbonylation raw materials are introduced into a carbonylation reactor 1. Acetic acid as a reaction solvent circulates between the carbonylation reactor 1 and a flasher 2. A bottom liquid of the flasher 2 mainly including acetic acid returns to the carbonylation reactor 1. A vapor phase fraction from the flasher 2 flows into a light end distillation column 4, and separation is performed inside the light end distillation column 4. The acetic acid is separated and recovered from the lower part of the light end distillation column 4, and components other than the acetic acid, and the acetic acid part that has not been recovered, are distilled off from the top part.

In the carbonylation reactor 1, the catalyst for carbonylation of methanol according to the present invention is dispersed and exists in the reaction solvent.

Methanol reacts with carbon monoxide to produce acetic acid. In this case, a reaction accelerator such as an alkyl iodide (for example, methyl iodide) is suitably added. This reaction is usually performed by using acetic acid as a reaction solvent, and in this case, the acetic acid is a reaction product and also serves as a reaction solvent. For example, carbon monoxide gas is blown into the reaction mixture in the carbonylation reactor 1 in which the catalyst for carbonylation of methanol according to the present invention has been dispersed, and in the presence of the catalyst for carbonylation of methanol according to the present invention under the conditions of a reaction temperature of 100 to 200° C. and a reaction pressure of around 1 to 5 MPa, methanol reacts with carbon monoxide to produce acetic acid. In this reaction, as the reaction by-products, methyl acetate, dimethyl ether, water and the like are produced, these by-products are returned to the reaction step together with the solvent, the reaction accelerator and unreacted raw materials as a residual liquid after the acetic acid has been separated and recovered as a product, therefore, the liquid phase in the reaction step includes a mixture of all of these components.

The reaction product solution produced in the reaction step is subjected to separation operation in the following distillation step, the produced acetic acid is separated and recovered as a product, a part of the residual liquid other than the recovered acetic acid is returned to the reaction step, and the rest is transferred to the standing step. For example, the reaction mixture is taken out from a carbonylation reactor 1 as the reaction step through a screen or the like and flows into a flasher 2. In the distillation step, a technique in which at first, a part of the reaction mixture is vaporized in the flasher 2 to separate into a vapor phase and a liquid phase (flash evaporation step), and then the vapor phase fraction is guided from the upper part of the flasher 2 to a light end distillation column 4, and the acetic acid is separated and recovered from the lower part (light end separation step) is adopted. The reason why such a technique is adopted is because the reaction product solution is a mixture of various kinds of components as described above, and acetic acid is a component having a low volatility among them, however, impurities having a lower volatility (or non-volatility) are mixed, therefore, the acetic acid cannot be recovered simply as a product from the bottom liquid. The flasher 2 and the light end distillation column 4 may be configured separately as separate towers as shown in FIG. 1, or may be integrally arranged in the bottom part and upper part of a single tower. In addition, since the carbonylation reaction is generally an exothermic reaction, by vaporizing a part in the flasher 2, an effect that the liquid phase fraction to be returned to the reaction step is cooled can be obtained, and further by introducing the heated reaction product solution to the flasher 2, the flasher 2 can function as an evaporator for the light end distillation column 4.

In the light end distillation column 4, a gas phase fraction is separated. By setting a part of the acetic acid having the lowest volatility among the components constituting the gas phase fraction to be accumulated in the lower part of the light end distillation column 4, all of the other gas phase components can be contained in an overhead fraction. The acetic acid is taken out from the lower part of the light end distillation column 4, subjected to a necessary purification treatment, and then separated and recovered as a product. On the other hand, the effluent from the overhead is introduced into a decanter 5.

The overhead effluent of the light end distillation column 4, which is introduced into a decanter 5 after the separation of acetic acid in the distillation step, contains methyl iodide, methyl acetate, and water as the main components. By allowing the effluent to stand in the decanter 5, methyl iodide contained in the effluent is separated as a heavy oil phase, and an aqueous phase is obtained. The separated methyl iodide is returned to the carbonylation reactor 1.

Further, the part not vaporized in the flasher 2 is accumulated as a liquid phase fraction in the bottom part of the flasher 2, and is returned as a bottom liquid from the distillation step (that is, a liquid phase fraction from the flasher 2) to the carbonylation reactor 1 in which a reaction step is performed.

Since the catalyst for carbonylation of methanol according to the present invention has high activity, acetic acid can be efficiently produced in the above-described method for producing acetic acid.

In addition, since the catalyst for carbonylation of methanol according to the present invention is excellent in the abrasion resistance, as a carbonylation reactor 1 in which a reaction step is performed, a stirred tank type reactor or a bubble column type reactor, which fluidizes a catalyst, can be used. That is, when acetic acid is produced, the catalyst for carbonylation of methanol according to the present invention can be reacted with carbon monoxide by bringing the catalyst into contact with the carbon monoxide while flowing with the reaction mixture in a reactor, and a stirring-type reactor or a bubble-type reactor can be used as the reactor.

Further, since the catalyst for carbonylation of methanol according to the present invention is also excellent in the heat resistance, the reaction temperature of the carbonylation reaction can be increased. Therefore, acetic acid can be produced in a stable amount by changing the reaction temperature in accordance with the state of the reaction, and the catalyst life can be prolonged.

For example, due to the equipment trouble in a purification system of a distillation step or the like, the delay in condition follow-up accompanying the changes in reaction conditions of carbonylation reaction, or the like, the water concentration of the reaction mixture may be increased. When the water concentration is increased, the solid-liquid equilibrium of rhodium in a catalyst is changed, so that rhodium is easily eluted into the reaction mixture, the catalytic activity is lowered, the production quantity of acetic acid is decreased, further, methyl acetate as a by-product is increased, the decomposition rate of the catalyst is increased, and the catalyst life is shortened. Note that methyl acetate is produced by a side reaction of $CH_3COOH+CH_3OH \rightarrow CH_3COOCH_3+H_2O$.

However, since the catalyst for carbonylation of methanol according to the present invention is excellent in the heat resistance, the reaction temperature can be increased. Specifically, when the water concentration of a reaction mixture is increased, the temperature of the reaction mixture is temporarily increased by a heat exchanger or the like installed in a reactor or outside the reactor. If the reaction temperature is increased when the water concentration of the reaction mixture is increased in this way, the catalytic activity is increased. Therefore, the decrease in the production quantity of acetic acid is suppressed, and acetic acid can be produced in a stable amount. In addition, by increasing the temperature of a reaction mixture, rhodium is hardly eluted into the reaction mixture, and since methanol is consumed as the catalytic activity is increased, hydrolysis of methyl acetate proceeds and the water concentration and the methyl acetate are decreased. Therefore, rhodium is adsorbed to a catalyst and the catalytic activity is restored, and the decomposition rate of the catalyst can also be lowered by reducing the methyl acetate. After the catalytic activity is thus restored and the decomposition rate of the catalyst is lowered, the reaction temperature is allowed to decrease, and the reaction is allowed to proceed under ordinary conditions. That is, when acetic acid is produced by using the catalyst for carbonylation of methanol according to the present invention, a step of increasing the temperature of a reaction mixture when the water concentration of the reaction mixture is increased may be included, and after the step of increasing the temperature of the reaction mixture when the water concentration of the reaction mixture is increased, a step of decreasing the temperature of the reaction mixture when the water concentration is decreased may be included.

EXAMPLES

Hereinafter, the present invention will be described by way of Examples for a better understanding of the present invention, but should not be limited at all by these Examples.

1. Preparation of Vinylpyridine Resin

Example 1

Into ion exchanged water, 10% by mass of NaCl (specific gravity adjusting agent), 0.3% by mass of $NaNO_2$ (radical scavenger), 0.064% by mass of gelatin (dispersion stabilizer), and 0.009% by mass of sodium dodecylbenzenesulfonate (surfactant) were dissolved to prepare 625 g of an aqueous medium.

Further, 375 g of a mixture in which 42.5% by mass of 4-vinylpyridine (vinylpyridine monomer), 37.5% by mass of divinylbenzene ((crosslinking agent), purity: 96% by mass, and the remainder is ethylvinylbenzene), 10% by mass of toluene (pore forming agent), 5% by mass of dioctyl phthalate (pore forming agent), and 5% by mass of n-dodecane (pore forming agent) had been mixed was prepared. Into the obtained mixture, relative to 100% by mass of the total amount of the monomers (total amount of 4-vinylpyridine, divinylbenzene, and ethylvinylbenzene) contained in the obtained mixture, 0.18% by mass of benzoyl peroxide (main polymerization initiator), and 0.07% by mass of 2,2'-azobis (2,4-dimethylvaleronitrile) (auxiliary polymerization initiator) were dissolved to prepare an oil medium. The oil medium was placed into a 1000-ml suspension polymerization reactor with a jacket. The prepared aqueous medium was supplied to the reactor from the lower part thereof, and the resultant mixture was slowly stirred. Note that this 1000-ml suspension polymerization reactor with a jacket was a stirred-tank reactor having a stirrer inside the reactor.

After stirring at 25° C. until oil droplets were uniformly dispersed, warm water at 65° C. was introduced into the jacket of the reactor to increase the temperature of the mixture in the reactor and the polymerization was performed. Since this polymerization was an exothermic reaction, reaction heat was generated, however, by adjusting the temperature of the warm water flowing in the jacket of the reactor, the increase in the temperature of the mixture in the reactor was suppressed, and the temperature of the mixture in the reactor was adjusted to be in the range of 64° C. to 66° C. After maintaining this state for 3 hours, the temperature of the warm water flowing in the jacket of the reactor was increased to 90° C. to increase the temperature of the mixture in the reactor to 85° C. or more, and the mixture was maintained for 4 hours as it was. After that, the temperature of the warm water flowing in the jacket of the reactor was set to 25° C. to cool the mixture in the reactor to room temperature, and then the mixture was subjected to solid-liquid separation by filtration to recover the produced resin. The produced resin was washed with warm water, further methanol was added to the washed resin to perform extraction and washing at 65° C., and toluene, dioctyl phthalate and n-dodecane, which are pore forming agents, were removed. After that the resultant mixture was sieved, and finally a 4-vinylpyridine resin for a catalyst support was obtained. The obtained 4-vinylpyridine resin for a catalyst support was spherical.

Examples 2 to 14 and Comparative Examples 1 to 7

A 4-vinylpyridine resin for a catalyst support was obtained in a similar manner as in Example 1 except that the divinylbenzene (crosslinking agent), the kind and ratio of the pore forming agent, the polymerization temperature, and the amount of the polymerization initiator to be added were set as shown in Table 1. In Table 1, the degree of crosslinking, and the absolute value (SP absolute difference) of the difference between the SP value of the vinylpyridine resin for a catalyst support and the SP value of the pore forming agent are also described. The vinylpyridine resin for a catalyst support of Comparative Example 1 corresponds to the vinylpyridine resin described in Patent Literature 7. The 4-vinylpyridine resins for a catalyst support obtained in respective Examples 2 to 14 and Comparative Examples 1 to 7 were spherical, respectively.

2. Measurement of Physical Properties

The physical properties of the obtained 4-vinylpyridine resin for a catalyst support were measured by the following method.
(1) Specific surface area, Total pore volume, Proportion of the volume of pores having a pore diameter of 10 nm or more to the volume of whole pores, Measurement of average pore diameter The specific surface area, the total pore volume, the proportion of the volume of pores having a pore diameter of 10 nm or more to the volume of the whole pores, and the average pore diameter of the obtained 4-vinylpyridine resin for a catalyst support were measured by the above-described method using AUTOSORB-1 manufactured by Yuasa Ionics Co., Ltd. As to the specific surface area, the specific surface area (total) of the whole vinylpyridine resin, and the specific surface of only the pores having a pore diameter of 2.0 nm or less (≤2 nm) was determined, and further the proportion (ratio (%)) of the specific surface area of only the pores having a pore diameter of 2.0 nm or less to the whole specific surface area was determined. The results are shown in Table 2.
(2) Analysis of Resin Composition The amounts of carbon, hydrogen, and nitrogen contained in the resin were analyzed by a CHN corder, and from the obtained values, the content of nitrogen (N content), and the molar ratio (C/N ratio) of the carbon atom to the nitrogen atom was determined. The results are shown in Table 1.
(3) Measurement of Powdering Ratio The obtained 4-vinylpyridine resin for a catalyst support was collected in an amount of 17 g (dry), 100 g of a 17% by mass methyl iodide methanol solution was added into the collected resin, and the resultant mixture was subjected to shaking for 18 hours to quaternize pyridine groups.

The quaternized 4-vinylpyridine resin for a catalyst support was placed into a 300 ml cylindrical separable flask (with 4 baffles), and stirred with a 40 mm disk turbine stirring blade at a stirring speed of 1000 rpm for 18, 72, and 144 hours.

After completion of the stirring, the resultant mixture was subjected to solid-liquid separation by a sieve with a mesh size of 90 μm, the passed liquid was received in a 300-ml beaker with a known mass, evaporated and dried at 90° C., and the mass was measured to be taken as a powdered substance. The powdering ratio was determined by the ratio of the mass of the obtained powdered substance to the mass of the charged 4-vinylpyridine resin for a catalyst support. In addition, the powdering rate was determined from the powdering ratios (%) after the lapse of 72 hours and 144 hours and the stirring time, and the average value thereof was taken as the respective powdering rates.
(4) Measurement of Catalytic Activity
(i) Catalyst Preparation The obtained 4-vinylpyridine resin for a catalyst support in an amount of 8.5 g (dry basis), 79.7 g of a reaction mixture (31.3% by mass of methanol, 21.6% by mass of methyl iodide, and 47.1% by mass of acetic acid), and an appropriate amount of rhodium acetate were charged into a 200-ml zirconium autoclave, and the catalyst was prepared by the reaction at a temperature of 180° C. and a CO pressure of 5.0 MPaG for one hour. As a result of analysis of the mixture after completion of the reaction by ICP emission spectroscopy, the ratio of the rhodium remaining in the reaction mixture was 0.2% by mole or less (supporting ratio of 99.8% by mole or more).
(ii) Reaction Test The total amount of the above-described catalyst, 80 g of a reaction mixture (25% by mass of methanol, 62.5% by mass of acetic acid, and 12.5% by mass of methyl iodide) were charged into a 200-ml zirconium autoclave, the carbonylation reaction was performed at a reaction temperature of 180° C. and a CO pressure of 5.0 MPaG for one hour, and the CO consumption rate at the time point when 60% by mole of the charged methanol had reacted was taken as the carbonylation reaction rate (STY: mol/L/h). Further, by setting the STY of Comparative Example 1 as 1.00, the ratio of carbonylation reaction rate was determined as the value for the STY of Comparative Example 1.

(5) Measurement of Thermal Decomposition Rate

The catalyst was prepared from the obtained 4-vinylpyridine resin by the method described above, the catalyst was charged into a 200-ml zirconium autoclave together with 100 ml of a solution of 8.0% by mass of methyl iodide, 5.5% by mass of water, and 86.5% by mass of acetic acid, and after replacing the air in the autoclave with nitrogen, the resultant mixture was heated to 220° C. while stirring. After that, the state at 220° C. was maintained while stirring the mixture in the autoclave, the mixture was collected after the lapse of 24 hours and the nitrogen concentration was measured to determine the amount of released pyridine groups. In addition, the nitrogen concentration in the obtained 4-vinylpyridine resin for a catalyst support was separately measured, and the ratio to the above-described amount of released pyridine groups determined by collecting the mixture after the lapse of 24 hours (the amount (mol) of left pyridine groups/the amount (mol) of nitrogen in the obtained 4-vinylpyridine resin for a catalyst support) was determined, and the ratio was divided by the decomposition time (24 hours) to determine the thermal decomposition rate.

Figure 2:
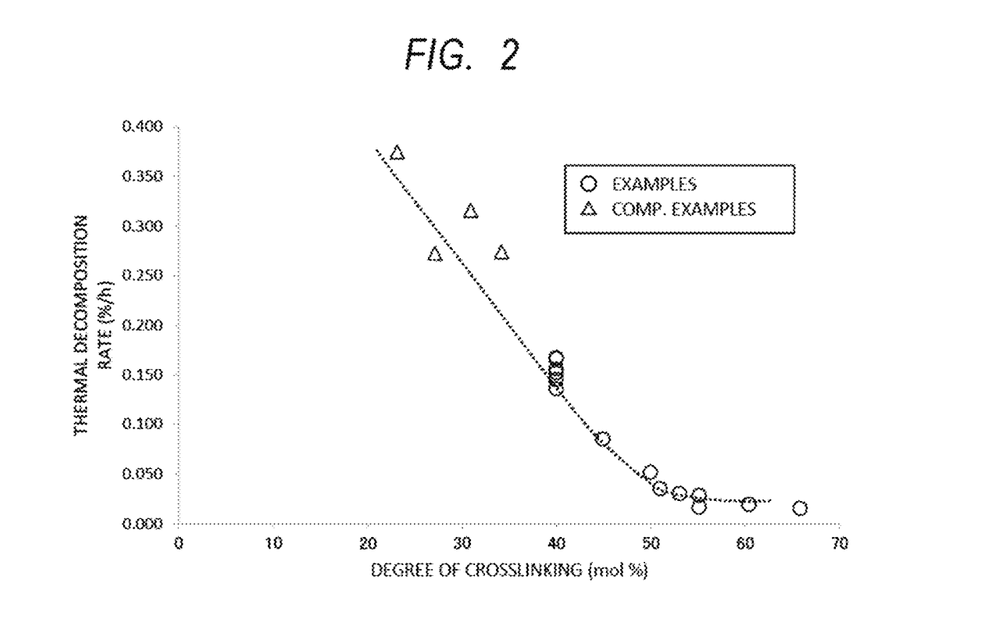
FIG. 2 is a diagram showing a relationship between the thermal decomposition rate and the degree of crosslinking in each of the examples and comparative examples.

The physical properties of the obtained 4-vinylpyridine resin for a catalyst support are shown in Tables 1 and 2. Note that in Tables 1 and 2, the purity of divinylbenzene is denoted by "DVB purity", the content of the nitrogen derived from pyridine groups is denoted by "N content", the molar ratio C/N of carbon atoms to nitrogen atoms is denoted by "C/N ratio", the trimethyl benzene is denoted by TMB, the dioctyl phthalate is denoted by DOP, the 2,2'-azobis(2,4-dimethylvaleronitrile) is denoted by V65, and the benzoyl peroxide is denoted by BPO. In addition, from the obtained results, the relationship between the thermal decomposition rate and the degree of crosslinking is shown in FIG. 2.

In this regard, in Comparative Examples 4 and 6, the carbonylation reaction was not generated because the catalytic activity was presumably low and in Comparative Example 5, the abrasion resistance was low and the decomposition and the powderizing were caused during the carbonylation reaction. Therefore, in both cases, the STY ratio, the thermal decomposition rate, and the powdering rate were not able to be determined.

The 4-vinylpyridine resins for a catalyst support obtained in Example 1 and Comparative Example 1 were subjected to the following operation and evaluation. The obtained 4-vinylpyridine resin for a catalyst support in an amount of 25.5 g (dry basis), 1000 g of a reaction mixture (31.3% by mass of methanol, 21.6% by mass of methyl iodide, and 47.1% by mass of acetic acid), and an appropriate amount of rhodium acetate were charged into a 2000-ml zirconium autoclave, and the reaction was performed at a reaction temperature of 180° C. and a CO pressure of 5.0 MPaG for one hour for the catalyst preparation. Next, the obtained catalyst was charged into a 2000-ml zirconium autoclave together with 1000 ml of a solution of 8.0% by mass of methyl iodide, 5.5% by mass of water, and 86.5% by mass of acetic acid, and after replacing the air in the autoclave with nitrogen, the resultant mixture was heated to 220° C. while stirring. After that, a catalyst at the target decomposition ratio was obtained by maintaining the state at 220° C. for the time to reach the target decomposition ratio (10 to 30%) while stirring in the autoclave (described in the column of "Time (hr)" in Tables). The nitrogen concentration of the mixture was measured to determine the amount of released pyridine groups, and the decomposition ratio was confirmed.

Figure 3:
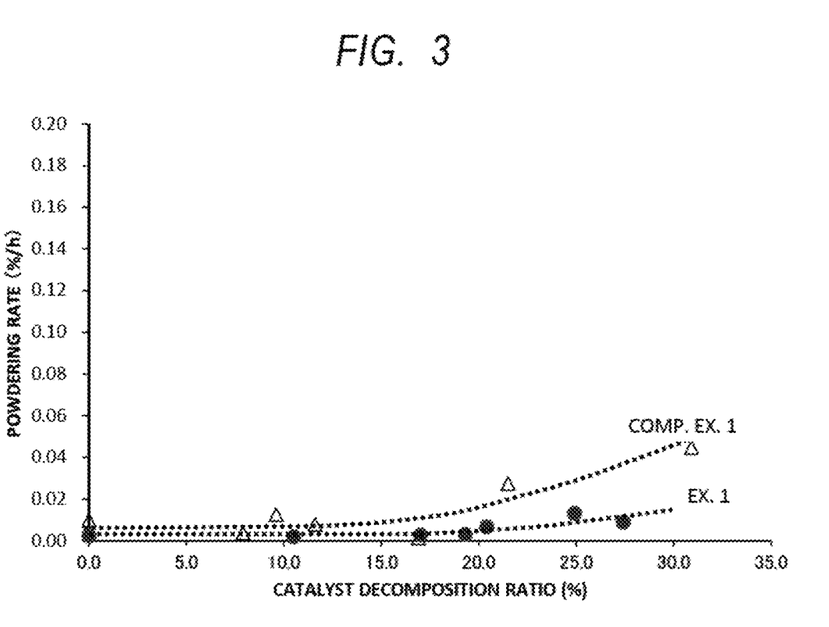
FIG. 3 is a diagram showing a relationship between the catalyst decomposition ratio and the powdering rate in each of Example 1 and Comparative Example 1.

A catalyst having a different decomposition ratio obtained by the above-described method was collected in an amount corresponding to 17 g (dry basis) of the 4-vinylpyridine resin, placed into a 300 ml cylindrical separable flask (with 4 baffles), and stirred with a 40 mm disk turbine stirring blade at a stirring speed of 250 rpm for 18, 72, and 144 hours. After completion of the stirring, the resultant mixture was subjected to solid-liquid separation by a sieve with a mesh size of 90 μm, the passed liquid was received in a 300-ml beaker with a known mass, evaporated and dried at 90° C., and the mass was measured to be taken as a powdered substance. The powdering ratio was determined by the ratio of the mass of the obtained powdered substance to the mass of the charged catalyst. In addition, the powdering rate was determined from the powdering ratios (%) after the lapse of 72 hours and 144 hours and the stirring time, the average value thereof was taken as the respective powdering rates, and the relationship with the catalyst decomposition ratio was determined. The results are shown in Table 3 (Example 1) and Table 4 (Comparative Example 1), and FIG. 3.

Figure 4:
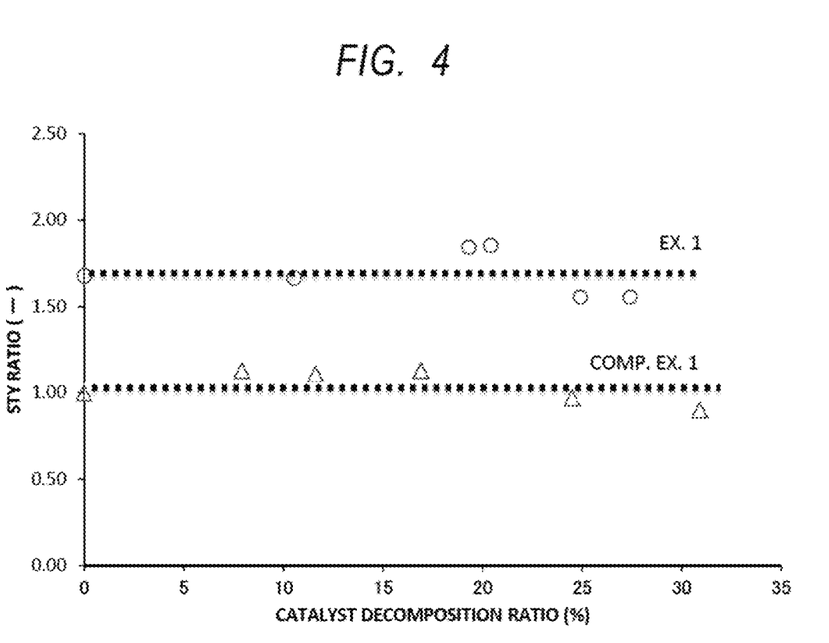
FIG. 4 is a diagram showing a relationship between the catalyst decomposition ratio and the catalytic activity in each of Example 1 and Comparative Example 1.

A catalyst having a different decomposition ratio obtained by the above-described method was collected in an amount corresponding to 8.5 g (dry basis) of the 4-vinylpyridine resin, and the activity was determined by a reaction test described above and the relationship between the catalyst decomposition ratio and the catalytic activity was determined. The results are shown in Table 5 (Example 1) and Table 6 (Comparative Example 1), and FIG. 4.

As shown in Tables 1 and 2, the vinylpyridine resins of Examples 1 to 14, which satisfy all of the requirements that: the content of the nitrogen derived from vinylpyridine groups is 3.00% by mass or more and 8.00% by mass or less, the degree of crosslinking is 35% by mole or more and 70% by mole or less, the molar ratio C/N of carbon atoms to nitrogen atoms is 12.00 or more and 36.00 or less, the total pore volume is 0.20 cc/g or more and 0.45 cc/g or less, the specific surface area is 70 m$^2$/g or more and 280 m$^2$/g or less, the average pore diameter is 5.0 nm or more and 25.0 nm or less, and the proportion of the volume of pores having a pore diameter of 10 nm or more to the volume of the whole pores is 4.0% or more and 90.0% or less were excellent in the heat resistance, the abrasion resistance and the catalytic activity. On the other hand, in a case where even if some of the above-described requirements are satisfied, but there is even one requirement being not satisfied, as shown in Comparative Examples 1 to 7, a vinylpyridine resin that is excellent in the heat resistance, the abrasion resistance and the catalytic activity was not able to be obtained.

TABLE 1

| | Degree of crosslinking (mol %) | DVB purity (wt %) | N content (wt %) | C/N ratio (mol/mol) | Pore forming agent (wt %) | | | | | SP absolute difference | Initiator (wt %) | | Polymerization temperature (° C.) |
|---|---|---|---|---|---|---|---|---|---|---|---|---|---|
| | | | | | Toluene | TMB | Octan | DOP | n-Dodecane | | V65 | BPO | |
| Example 1 | 40 | 96 | 7.08 | 14.12 | 10 | — | — | 5 | 5 | 2.22 | 0.07 | 0.18 | 65 |
| Example 2 | 40 | 96 | 7.08 | 14.12 | — | 10 | — | 5 | 5 | 2.41 | 0.07 | 0.18 | 65 |
| Example 3 | 40 | 96 | 7.08 | 14.12 | — | 10 | 7 | 3 | — | 2.64 | 0.15 | 0.37 | 65 |

TABLE 1-continued

| | Degree of crosslinking (mol %) | DVB purity (wt %) | N content (wt %) | C/N ratio (mol/mol) | Pore forming agent (wt %) | | | | | SP absolute difference | Initiator (wt %) | | Polymerization temperature (° C.) |
|---|---|---|---|---|---|---|---|---|---|---|---|---|---|
| | | | | | Toluene | TMB | Octan | DOP | n-Dodecane | | V65 | BPO | |
| Example 4 | 40 | 96 | 7.08 | 14.12 | 10 | — | — | 5 | 5 | 2.22 | 0.17 | 0.18 | 65 |
| Example 5 | 40 | 96 | 7.08 | 14.12 | — | 10 | — | 3 | 7 | 2.46 | 0.24 | 0.61 | 65 |
| Example 6 | 40 | 96 | 7.08 | 14.12 | — | 12 | 6 | 2 | — | 2.41 | 0.24 | 0.61 | 65 |
| Example 7 | 45 | 96 | 6.39 | 15.77 | 10 | — | — | 5 | 5 | 2.08 | 0.07 | 0.18 | 65 |
| Example 8 | 50 | 96 | 5.69 | 17.82 | 10 | — | — | 5 | 5 | 1.95 | 0.07 | 0.18 | 65 |
| Example 9 | 51 | 96 | 5.56 | 18.29 | 10 | — | — | — | 10 | 2.04 | 0.07 | 0.18 | 65 |
| Example 10 | 53 | 96 | 5.28 | 19.31 | 10 | — | — | — | 10 | 1.98 | 0.07 | 1.00 | 70 |
| Example 11 | 55 | 96 | 5.00 | 20.45 | — | 10 | — | 5 | 5 | 2.01 | 0.07 | 0.18 | 65 |
| Example 12 | 55 | 96 | 5.00 | 20.45 | — | 10 | — | 5 | 5 | 2.07 | 0.07 | 1.00 | 65 |
| Example 13 | 60 | 96 | 4.31 | 23.92 | 8 | — | — | 1 | 12 | 1.90 | 0.21 | 0.75 | 70 |
| Example 14 | 66 | 96 | 3.61 | 28.72 | 8 | — | — | 1 | 12 | 1.80 | 0.21 | 0.75 | 70 |
| Comparative Example 1 | 27 | 56 | 6.19 | 16.20 | — | 15 | — | 5 | — | 1.72 | 0.34 | 0.84 | 65 |
| Comparative Example 2 | 31 | 80 | 7.60 | 13.24 | 12 | — | 8 | — | — | 1.91 | 0.38 | 0.92 | 70 |
| Comparative Example 3 | 34 | 96 | 7.78 | 12.76 | 10 | — | 8 | — | — | 2.57 | 0.38 | 0.92 | 68 |
| Comparative Example 4 | 55 | 96 | 5.00 | 20.45 | — | 20 | — | — | — | 1.13 | 0.07 | 0.18 | 65 |
| Comparative Example 5 | 55 | 96 | 5.00 | 20.45 | — | — | — | — | 20 | 2.77 | 0.07 | 0.18 | 65 |
| Comparative Example 6 | 55 | 96 | 5.00 | 20.45 | 10 | — | — | 10 | — | 1.63 | 0.07 | 0.18 | 65 |
| Comparative Example 7 | 23 | 56 | 7.14 | 13.91 | — | 15 | — | 5 | — | 1.96 | 0.21 | 0.84 | 65 |

TABLE 2

| | Specific surface area (m2/g) | | | Total pore volume (cc/g) | Average pore diameter (nm) | Pores having a pore diameter of 10 nm or more | | STY (mol/L × h) | STY ratio (—) | Thermal decomposition rate (%/h) | Powdering rate (%/h) |
|---|---|---|---|---|---|---|---|---|---|---|---|
| | Total | ≤2 nm | Ratio (%) | | | Total volume (cc/g) | Proportion of the volume of pores to the volume of the whole pores (%) | | | | |
| Example 1 | 76.4 | 44.30 | 57.98 | 0.28 | 14.8 | 0.24 | 83.9 | 15.1 | 1.68 | 0.15 | 0.02 |
| Example 2 | 73.6 | 28.64 | 38.91 | 0.32 | 17.2 | 0.28 | 87.5 | 15.9 | 1.77 | 0.15 | 0.05 |
| Example 3 | 75.5 | 22.29 | 29.52 | 0.20 | 14.2 | 0.17 | 85.0 | 14.6 | 1.62 | 0.17 | 0.02 |
| Example 4 | 74.4 | 23.35 | 31.38 | 0.25 | 13.5 | 0.20 | 80.0 | 15.1 | 1.68 | 0.16 | 0.02 |
| Example 5 | 78.7 | 35.29 | 44.84 | 0.29 | 14.6 | 0.24 | 82.8 | 14.8 | 1.64 | 0.17 | 0.06 |
| Example 6 | 89.7 | 30.68 | 34.20 | 0.24 | 10.5 | 0.21 | 77.8 | 14.2 | 1.58 | 0.14 | 0.04 |
| Example 7 | 76.7 | 21.29 | 27.76 | 0.24 | 12.6 | 0.16 | 66.7 | 14.0 | 1.56 | 0.09 | 0.03 |
| Example 8 | 79.4 | 15.89 | 20.01 | 0.24 | 11.9 | 0.13 | 54.2 | 13.4 | 1.49 | 0.05 | 0.04 |
| Example 9 | 112.0 | 42.21 | 37.69 | 0.35 | 12.6 | 0.26 | 74.9 | 14.0 | 1.56 | 0.04 | 0.03 |
| Example 10 | 150.0 | 35.38 | 23.58 | 0.28 | 7.5 | 0.05 | 17.9 | 12.2 | 1.36 | 0.03 | 0.02 |
| Example 11 | 108.1 | 20.82 | 19.26 | 0.26 | 9.5 | 0.06 | 23.1 | 12.0 | 1.33 | 0.02 | 0.06 |
| Example 12 | 151.0 | 19.82 | 13.13 | 0.21 | 5.6 | 0.01 | 4.2 | 10.5 | 1.17 | 0.03 | 0.04 |
| Example 13 | 181.0 | 73.90 | 40.83 | 0.37 | 8.1 | 0.19 | 51.4 | 12.4 | 1.38 | 0.02 | 0.06 |
| Example 14 | 276.0 | 114.00 | 41.30 | 0.40 | 5.8 | 0.07 | 17.0 | 9.8 | 1.09 | 0.02 | 0.03 |
| Comparative Example 1 | 60.1 | 2.00 | 3.33 | 0.11 | 7.2 | 0.01 | 9.3 | 9.0 | 1.00 | 0.27 | 0.05 |
| Comparative Example 2 | 67.2 | 21.71 | 32.31 | 0.26 | 15.4 | 0.23 | 88.5 | 14.2 | 1.58 | 0.32 | 0.05 |
| Comparative Example 3 | 65.7 | 11.84 | 18.02 | 0.21 | 12.1 | 0.15 | 71.4 | 13.7 | 1.52 | 0.27 | 0.01 |
| Comparative Example 4 | 4.2 | 2.70 | 64.29 | 0.03 | 1.1 | 0.00 | 6.7 | — | — | — | — |
| Comparative Example 5 | 108.5 | 57.87 | 53.34 | 0.72 | 26.5 | 0.65 | 90.3 | — | — | — | — |
| Comparative Example 6 | 2.6 | 1.60 | 61.54 | 0.01 | 2.8 | 0.00 | 20.0 | — | — | — | — |
| Comparative Example 7 | 39.4 | 12.20 | 30.96 | 0.21 | 20.9 | 0.20 | 95.1 | 12.8 | 1.42 | 0.38 | 0.02 |

TABLE 3

| Time (hr) | Catalyst decomposition ratio (%) | Powdering rate (%/h) |
|---|---|---|
| 0 | 0.0 | 0.0025 |
| 96 | 10.5 | 0.0020 |
| 117 | 17.0 | 0.0029 |
| 120 | 19.3 | 0.0031 |
| 144 | 20.4 | 0.0067 |
| 168 | 24.9 | 0.0132 |
| 192 | 27.4 | 0.0090 |

TABLE 4

| Time (hr) | Catalyst decomposition ratio (%) | Powdering rate (%/h) |
|---|---|---|
| 0 | 0 | 0.0100 |
| 36 | 7.9 | 0.0039 |
| 48 | 9.6 | 0.0127 |
| 48 | 11.6 | 0.0079 |
| 72 | 16.9 | 0.0014 |
| 84 | 21.5 | 0.0276 |
| 120 | 30.9 | 0.0448 |

TABLE 5

| Time (hr) | Catalyst decomposition ratio (%) | STY ratio (—) |
|---|---|---|
| 0 | 0 | 1.68 |
| 96 | 10.5 | 1.67 |
| 120 | 19.3 | 1.84 |
| 144 | 20.4 | 1.86 |
| 168 | 24.9 | 1.56 |
| 192 | 27.4 | 1.56 |

TABLE 6

| Time (hr) | Catalyst decomposition ratio (%) | STY ratio (—) |
|---|---|---|
| 0 | 0 | 1.00 |
| 36 | 7.9 | 1.13 |
| 48 | 11.6 | 1.11 |
| 72 | 16.9 | 1.13 |
| 96 | 24.5 | 0.97 |
| 120 | 30.9 | 0.90 |

The present application claims a priority based on Japanese Patent Application No. 2016-54644 filled on Mar. 18, 2016 in Japan, and all of the contents are incorporated herein by reference.

REFERENCE SIGNS LIST 1 carbonylation reactor
2 flasher
4 light end distillation column
5 decanter

The invention claimed is:

1. A vinylpyridine resin for a catalyst support, having:
a content of nitrogen in pyridine groups of the vinylpyridine resin of 3.00% by mass or more and 8.00% by mass or less; a degree of crosslinking of 35% by mole or more and 70% by mole or less; a molar ratio C/N of carbon atoms to nitrogen atoms of 12.00 or more and 36.00 or less; a total pore volume of 0.20 cc/g or more and 0.45 cc/g or less; a specific surface area of 70.0 $m^2/g$ or more and 280 $m^2/g$ or less; an average pore diameter of 5.0 nm or more and 25.0 nm or less; and a proportion of a volume of pores having a pore diameter of 10 nm or more to a volume of the whole pores of 4.0% or more and 90.0% or less,
wherein the vinylpyridine resin is a copolymer of vinylpyridine and divinylbenzene.

2. A method for producing a vinylpyridine resin for a catalyst support according to claim 1, the method comprising:
mixing an oil medium containing vinylpyridine, a crosslinking agent, a pore forming agent and a polymerization initiator, and an aqueous medium; and subjecting the resultant mixture to suspension polymerization, wherein
the polymerization initiator contains a main polymerization initiator, and an auxiliary polymerization initiator having a half-life temperature lower than a half-life temperature of the main polymerization initiator, the auxiliary polymerization initiator is 0.25% by mass or less relative to the total amount of monomers, and
the pore forming agent contains two or more kinds of organic solvents, and an absolute value of difference between a SP value of the vinylpyridine resin for a catalyst support and a SP value of the pore forming agent is 1.80 or more and 2.80 or less.

3. The method for producing a vinylpyridine resin for a catalyst support according to claim 2, wherein
the main polymerization initiator is 1.50% by mass or less relative to the total amount of monomers.

4. The method for producing a vinylpyridine resin for a catalyst support according to claim 2, wherein
the pore forming agent contains an organic solvent having a benzene ring.

5. The method for producing a vinylpyridine resin for a catalyst support according to claim 2, wherein
the auxiliary polymerization initiator has a half-life temperature lower than a temperature of the suspension polymerization, and
the main polymerization initiator has a half-life temperature higher than a temperature of the suspension polymerization.

6. A catalyst for carbonylation of methanol, comprising supporting rhodium on the vinylpyridine resin for a catalyst support according to claim 1.

7. The catalyst for carbonylation of methanol according to claim 6, wherein
a thermal decomposition rate in a mixture of 86.5% by mass of acetic acid, 8.0% by mass of methyl iodide, and 5.5% by mass of water under a condition of 220° C. in a nitrogen atmosphere is 0.25% by mole or less per hour.

* * * * *